United States Patent [19]

Margalit

[11] Patent Number: 5,603,872
[45] Date of Patent: Feb. 18, 1997

[54] METHOD OF BINDING RECOGNIZING SUBSTANCES TO LIPOSOMES

[75] Inventor: Rimona Margalit, Givataim, Israel

[73] Assignee: Baxter International Inc., Deerfield, Ill.

[21] Appl. No.: 316,793

[22] Filed: Oct. 3, 1994

Related U.S. Application Data

[63] Continuation-in-part of Ser. No. 58,442, May 7, 1993, abandoned, Ser. No. 951,351, Sep. 25, 1992, abandoned, Ser. No. 960,196, Oct. 9, 1992, Pat. No. 5,401,511, and Ser. No. 978,985, Nov. 19, 1992, abandoned, which is a continuation-in-part of Ser. No. 655,013, Feb. 14, 1991, abandoned, said Ser. No. 58,442, is a continuation of Ser. No. 655,576, Feb. 14, 1991, abandoned, said Ser. No. 951,351, is a continuation of Ser. No. 655,879, Feb. 14, 1991, abandoned, said Ser. No. 960,196, is a continuation of Ser. No. 655,878, Feb. 14, 1991, abandoned.

[51] Int. Cl.$^6$ .................................. A61K 9/127; B01J 13/20
[52] U.S. Cl. ..................... 264/4.3; 424/1.21; 424/78.04; 424/78.06; 424/428; 424/450; 427/2.14; 428/402.2; 436/829; 514/62
[58] Field of Search ..................... 264/4.3; 428/402.2; 424/1.21, 78.04, 78.06, 450, 428; 427/2.14; 436/829; 514/62

[56] References Cited

U.S. PATENT DOCUMENTS

| | | | |
|---|---|---|---|
| 4,323,561 | 4/1982 | Nowotny | 514/62 |
| 4,376,059 | 3/1983 | Davis et al. | 264/4.3 |
| 4,429,008 | 1/1984 | Martin et al. | 428/402.2 |
| 4,480,041 | 10/1984 | Myles et al. | 436/829 X |
| 4,485,054 | 11/1984 | Mezei et al. | 264/4.6 |
| 4,515,736 | 5/1985 | Deamer | 264/4.3 |
| 4,704,355 | 11/1987 | Bernstein | 436/829 X |
| 4,708,861 | 11/1987 | Popescu et al. | 424/457 |
| 4,755,388 | 7/1988 | Heath et al. | 424/450 |
| 4,761,288 | 8/1988 | Mezei et al. | 424/450 |
| 4,767,615 | 8/1988 | Geho et al. | 424/57 |
| 4,839,175 | 6/1989 | Guo et al. | 424/450 |
| 4,859,538 | 8/1989 | Ribi | 428/474.4 |
| 4,885,172 | 12/1989 | Bally et al. | 424/450 X |
| 4,889,722 | 12/1989 | Sheffield et al. | 424/450 |
| 4,944,948 | 7/1990 | Uster et al. | 424/450 |
| 5,043,166 | 8/1991 | Barenholz et al. | 424/450 |
| 5,049,390 | 9/1991 | Wojdani | 424/450 |
| 5,244,672 | 9/1993 | Huc et al. | 424/450 |
| 5,366,958 | 11/1994 | Weiner et al. | 424/450 X |
| 5,401,511 | 3/1995 | Margalit | 424/450 |

FOREIGN PATENT DOCUMENTS

| | | |
|---|---|---|
| 31948/89 | 6/1991 | Australia. |
| 85742/91 | 4/1992 | Australia. |
| 36277 | 9/1981 | European Pat. Off.. |
| WO88/00824 | 2/1988 | WIPO. |
| WO89/11270 | 11/1989 | WIPO. |
| WO90/07924 | 7/1990 | WIPO. |
| WO90/09782 | 9/1990 | WIPO. |
| WO90/11069 | 10/1990 | WIPO. |
| WO92/13525 | 8/1992 | WIPO. |

OTHER PUBLICATIONS

Excerpt from *Patent Abstracts of Japan*, vol. 9, No. 74 (C–273) (1797), dated Apr. 3, 1985.

German publication authored by V. Weissig et al., titled, "Kovalente Bindug von Peptiden an Liposomale Oberflachen;" pp. 849–850 of *Pharmazie*, vol. 45, No. 11, dated Nov. 1990.

Chapter 6 of vol. III from *Liposome Technology* (Gregoriadis, Editor; CRC Press, Publisher, 1984); "Immobilization of Specific Proteins on Liposome Surface; Systems for Drug Targeting," chapter.

Publication from vol. 160, No. 2, 1989 of *Biochemical and Biophysical Research Communications*, titled, "Preparation of EGF Labeled Liposomes and Their Uptake by Hepatocytes."

Publication from *Ann. Rev. Biochem*, 1979, 48:193–216, titled, "Epidermal Growth Factor" (Carpenter and Cohen, authors).

Publication from *Proc. Natl. Acad. Sci. USA*, vol. 72, No. 4, pp. 1317–1321, Apr. 1975 (Cohen and Carpenter, authors) titled, "Human Epidermal Growth Factor: Isolation and Chemical and Biological Properties."

Article published by *Biochemical and Biophysical Research Communications*, vol. 140, No. 3, 1986, pp. 837–843, titled, "The Relationship Between Epidermal Growth Factor Receptors and the Terminal Differentiation of A431 Carcinoma Cells."

Article published by *Proc. Natl. Acad. Sci. USA*, vol. 80, Mar. 1986, pp. 1337–1341, titled, "Growth Stimulation of A431 Cells by Epidermal Growth Factor: Identification of High–Affinity Receptors for Epidermal Growth Factor by an Anti–Receptor Monoclonal Antibody."

Publication from *Methods in Enzymology*, vol. 70, 1980 (Reichlin, author; Academic Press, Inc., publisher), titled, "Use of Glutaraldehyde as a Coupling Agent for Proteins and Peptides."

Ostro: "Liposomes–from Biophysics to Therapeutics", Marcel Dekker, Inc., New York (1987), pp. 176–187.

*Primary Examiner*—Richard D. Lovering
*Attorney, Agent, or Firm*—Mark J. Buonaiuto; Monique Morneault

[57] ABSTRACT

Recognizing substances, including epidermal growth factor, gelatin, collagen and hyaluronic acid, have been covalently bound to liposomal surfaces and utilized to attach liposomes onto a cellular or an extracellular matrix (ECM) target site. These "bioadhesive" liposomes offer several advantages including the mutual protection of both the drug and biological environment; an increase in drug bioavailability and retention at the target site; and improved adherence or adhesion to the designated target site.

2 Claims, 3 Drawing Sheets

METHOD OF BINDING RECOGNIZING SUBSTANCES TO LIPOSOMES

REFERENCE TO RELATED APPLICATIONS

This is a Continuation-In-Part of: (a) U.S. patent application Ser. No. 08/058,442 filed May 7, 1993 and now abandoned, which is a Continuation of U.S. patent application Ser. No. 655,576 filed Feb. 14, 1991, now abandoned (b) U.S. patent application Ser. No. 07/951,351, filed Sep. 25, 1992, now abandoned which is a File Wrapper Continuation of U.S. patent application Ser. No. 655,879 filed Feb. 14, 1991, now abandoned; (c) U.S. patent application Ser. No. 07/960,196 filed Oct. 9, 1992, now U.S. Pat. No. 5,401,511 which is a File Wrapper Continuation of U.S. patent application Ser. No. 07/655,878 filed Feb. 14, 1991, now abandoned; and, (d) U.S. patent application Ser. No. 07/978,985 filed Nov. 19, 1992, now abandoned which is a Continuation-In-Part of U.S. patent application Ser. No. 655,013 filed Feb. 14, 1991, now abandoned.

BACKGROUND OF THE INVENTION

The present invention relates to the preparation of microscopic drug delivery systems (MDDS) utilizing drug-encapsulating bioadhesive liposomes.

Currently, the topical and local administration of a drug can be in its free form, dissolved or dispersed in a suitable diluent, or in a vehicle such as a cream, gel or ointment. By definition, "topical" administration includes non-invasive drug administration, while "local" includes invasive, i.e., through a localized injection or infusion. Examples of therapeutic or designated targets for topical or local drug administration include burns; wounds; bone injuries; ocular, skin, intranasal and buccal infections; ocular chronic situations such as glaucoma; intraperitoneal infections, tumors and metastasis; and topically and locally accessed tumors. Several difficulties exist with either the topical or local administration of a drug in its free form. For example, short retention of the drug at the designated site of administration reduces the efficacy of the treatment and requires frequent dosing. Exposure of the free form drug to the biological environment in the topical or local region can result in drug degradation, transformation into inactive entities and non-discriminating and uncontrollable distribution of the drug. Such degradation and uncontrollable distribution of the drug can result in toxicity issues, undesirable side effects and loss of efficacy.

Microscopic drug delivery systems (MDDS) have been developed for improved drug administration relative to administration of drugs in their free form. Drug-loaded MDDS can perform as sustained or controlled release drug depots. By providing a mutual protection of the drug and the biological environment, MDDS reduces drug degradation or inactivation. As a system for controlled release of a drug, MDDS improves drug efficacy and allows reduction in the frequency of dosing. Since the pharmacokinetics of free drug release from depots of MDDS are different than from directly-administered drug, MDDS provides an additional measure to reduce toxicity and undesirable side effects.

MDDS is divided into two basic classes: particulate systems, such as cells, microspheres, viral envelopes and liposomes; or nonparticulate systems which are macromolecules such as proteins or synthetic polymers. Liposomes have been studied as drug carriers and offer a range of advantages relative to other MDDS systems. Composed of naturally-occurring materials which are biocompatible and biodegradable, liposomes are used to encapsulate biologically active materials for a variety of purposes. Having a variety of layers, sizes, surface charges and compositions, numerous procedures for liposomal preparation and for drug encapsulation within them have been developed, some of which have been scaled up to industrial levels.

Liposomes can be designed to act as sustained release drug depots and, in certain applications, aid drug access across cell membranes. Their ability to protect encapsulated drugs and various other characteristics make liposomes a popular choice in developing MDDS, with respect to the previous practices of free drug administration.

Despite the advantages offered, utilization of drug-encapsulating liposomes does pose some difficulties. For example, liposomes as MDDS have limited targeting abilities, limited retention and stability in circulation, potential toxicity upon chronic administration and inability to extravasate. Binding of chymotrypsin to liposomes has been studied as a model for binding substances to liposomal surfaces. Recognizing substances, including antibodies, glycoproteins and lectins have been bound to liposomal surfaces in an attempt to confer target specificity to the liposomes. Concentrating on systemic applications and in vivo studies, these previous efforts discuss methods of binding recognizing substances with liposomes and the effectiveness of such modified liposomes. Although the bonding of these recognizing substances to liposomes occurred, the resulting modified liposomes did not perform as hoped, particularly during in vivo studies. Other difficulties are presented when utilizing these recognizing substances. For example, antibodies can be patient specific and, therefore, add cost to the drug therapy.

In addition to the problems outlined above, the prior art has failed to disclose an efficient and effective method of making bioadhesive liposomes useful for scaling-up to an industrial level. In "Preparation of EGF Labeled Liposomes and Their Uptake by Hepatocytes," Ishii et al., Biochemical and Biophysical Research Communications, Vol. 160, pp. 732–36, 1989 ("Ishii et al."), the authors describe uptake of EGF-bearing liposomes by liver cells in suspension. In the preparation of their liposomes, Ishii et al., disclose a procedure involving at least four different steps, each individually involving at least two more sub-steps. These steps include further purification by column chromatography, which can be difficult to scale-up to an industrial level. Furthermore, not only is this process cumbersome, but each additional step contributes to a loss of material or possible inactivation of the EGF. It has been reported that the biological activity of EGF is dependent upon the conservation of the native conformation of EGF, to which the disulfide bonds are critical. In binding EGF to liposomes, Ishii et al. exploited the existence of the disulfide bonds. Specifically, EGF was bound to the liposomal surface by the disulfide bridge linkage using a heterobifunctional crosslinking reagent, N-hydroxysuccinimidyl-3-(2-pyridyldithio) propionate. The complex chemistry of this process results in byproducts whose effect on drug delivery and toxicity are unknown, possibly resulting in inactivation of the EGF. Further, the complex process described by Ishii et al. would be virtually impossible to accomplish in an aseptic environment, as required in a liposome process.

Prior to the development of the present invention, a need existed for a liposome having targeting and retention abilities to a target organ or tissue. Specifically, there remains a need for the development of a "bioadhesive" liposome comprising a liposome having an effective recognizing substance attached thereto. Prior to the present invention, a need also existed for an efficient method for binding recognizing substances to a liposome thereby producing a bioadhesive liposome, using fewer steps than those described in the prior art.

SUMMARY OF INVENTION

According to the present invention, efficient methodologies have been developed to effectively bind various recognizing substances. These include, and are not limited to, collagen, gelatin, hyaluronic acid and epidermal growth factor to liposomal surfaces thereby forming bioadhesive liposomes. Further, the methods of the present invention employ fewer steps than known in the art, thus making such methods more efficient and cost-effective on a commercial scale. Further, the process described in the present invention avoids the risk of inactivating the recognizing substance during creation of the bioadhesive liposome. The bioadhesive liposomes of the present invention have specificity for and the ability to adhere to the designated target area for sustained release of the liposome's therapeutic contents.

The improved process of the present invention includes adding a recognizing substance to a liposome; adding a crosslinking reagent to the mixture of the liposome and recognizing substance; and, allowing the mixture to incubate for a period of time to form the bioadhesive liposome. By modifying regular liposomes through covalent bonding of certain recognizing substance to the liposomal surface, the recognizing substances can be utilized as an adhesive or glue to attach and retain the modified liposome onto a target area despite cellular and fluid dynamics. These "bioadhesive" liposomes offer potential advantages as a MDDS for the administration of drugs.

DETAILED DESCRIPTION

According to the present invention, various recognizing substances have been covalently bound to liposomal surfaces through the crosslinking of amine residues. Liposomes, in particular, multilamellar vesicles (MLV) or unilamellar vesicles such as microemulsified liposomes (MEL) and large unilamellar liposomes (LUVET), each containing phosphatidylethanolamine (PE), have been prepared by established procedures. The inclusion of PE in the liposome provides an active functional residue, a primary amine, on the liposomal surface for crosslinking purposes.

Recognizing substances have been successfully linked with PE-liposomes. Recognizing substances useful in the present invention include collagen, gelatin, hyaluronic acid (HA) and epidermal growth factor (EGF). Using commercially available gelatin and collagen, these protein-recognizing substances were linked to the liposomes through amine residues. Hyaluronic acid is a natural polymer with alternating units of N-acetyl glucoseamine and glucoronic acid. Using a crosslinking reagent, hyaluronic acid offers carboxylic acid residues as functional groups for covalent binding. The N-acetyl-glucoseamine contains hydroxyl units of the type —$CH_2$—OH which can be oxidized to aldehydes, thereby offering an additional method of crosslinking hyaluronic acid to the liposomal surface in the absence of a crosslinking reagent. EGF is a polypeptide. Although urogastrone and EGF are recognized as biological equivalents, both purified urogastrone or EGF mouse were used as recognizing substances. When used in the specification and claims, the term "EGF" means either urogastrone or epidermal growth factor regardless of the source.

EGF stimulates cell growth and proliferation through interaction with an EGF receptor. EGF receptors are distributed on the cell surface of various organs and are present in burns, wounds, and other designated targets of MDDS such as ocular, dermal and tumors. Accordingly, EGF-modified liposomes potentially offer efficiency as drug carriers to target sites, i.e., organs or tissues, expressing the EGF receptors.

Recognizing substances are bound covalently to discrete sites on the liposome surfaces. The number and surface density of these sites will be dictated by the liposome formulation and the liposome type. The liposomal surfaces may also have sites for noncovalent association. Covalent binding is essential as noncovalent binding might result in dissociation of recognizing substances from the liposomes at the site of administration since the liposomes and the bioadhesive counterparts of the target site (the bioadhesive matter) compete for the recognizing substances. Such dissociation would reverse the administered modified liposomes into regular, non-modified liposomes, thereby defeating the purpose of administration of the modified liposomes.

To form covalent conjugates of recognizing substances and liposomes, crosslinking reagents have been studied for effectiveness and biocompatibility. Crosslinking reagents include glutaraldehyde (GAD), bifunctional oxirane (OXR), ethylene glycol diglycidyl ether (EGDE), and a water soluble carbodiimide, preferably 1-ethyl-3-(3-dimethylaminopropyl) carbodiimide (EDC). Through the complex chemistry of crosslinking, linkage of the amine residues of the recognizing substance and liposomes is established.

An important feature of the present invention is the binding between the newly-created bioadhesive liposome and potential biological target sites. Biological target sites are divided into two classes. The first class encompasses components of the extracellular matrix (ECM). The ECM can be visualized as a network made of a variety of components, which is not cast loose in a living system, but is connected at some of its points to cells. ECM is found underneath cells, above cells, in between layers of cells, and in between cells in a layer. The second class of potential targets are membrane-embedded receptors.

A complete accounting of binding entities has been determined by the previously known multi-term Langmuir Isotherm equation, as applied for the quantitative description of the relationship between the free and dependent variables:

$$B = \sum_{i=1}^{n} \frac{Bmax_i [L]}{Kd_i + [L]} \quad (1)$$

where n is the number of different types of binding entities that a cellular or an ECM system target site has for a specific recognizing substance; [L] is the concentration of free ligand, which can be recognizing substance, free liposomes or bioadhesive liposomes; B is the total quantity of bound recognizing substance per given number of cells or quantity of ECM, at a given [L]; and, $Bmax_i$ and $Kd_i$ are the total number of sites of a given entity and the corresponding equilibrium dissociation constant. B and $B_{max}$ are normalized for the same number of cells or quantity of ECM.

For cases in which receptors and non-receptor cell membrane components participate in the recognizing substance binding and in which the dissociation constant of the non-specific binding is sufficiently large with respect to the free ligand concentration, equation 1 can take the form:

$$B = \sum_{i=1}^{n-1} \frac{Bmax_i [L]}{Kd_i + [L]} + K_{ns} [L] \quad (2)$$

where the last term, $K_{ns}$ [L], is the contribution of the non-specific binding to B and $K_{ns}$ is the ratio of Bmax to Kd corresponding to the non-specific binding.

"Best-fit" values for parameters n, $Bmax_i$ and $Kd_i$ are obtained by computer-aided data analysis, according to equations (1) and/or (2) above, applying procedures of nonlinear regression analysis.

The interaction of the bioadhesive liposomes with potential biological targets has been established through the use of cultures of A431 cells, in monolayers, as a biological model. This well-established cell line, originating from human epidermoid carcinoma, is enriched with EGF receptors, and as a monolayer, also provides ECM. A431 cells have been repeatedly used for study of the interaction of free EGF and its receptor. A431 cells have been shown to have three classes of EGF receptors, differing in their affinities and populations. The first of these classes is the ultra-high affinity sites with an equilibrium dissociation constant of 0.07 nM and a population of 150–4000 sites per cell. The next class is the high affinity sites with an equilibrium dissociation constant of 0.7 nM and a population of 1.5×10⁵ sites per cell. The final class is the low affinity sites with an equilibrium dissociation constant of 5.9 nM and a population of 2×10⁶ sites per cell. Because of their affinity for EGF, A431 is particularly useful for demonstrating the targeting ability of EGF-modified liposomes. However, targeting of bioadhesive liposomes having other types of recognizing substances has also been demonstrated with this cell line, as shown in the following Examples.

The "level of covalent binding" as reported in the Examples below is defined as the quantity of bioadhesive ligand, such as collagen, gelatin, hyaluronic acid or EGF bound to a given quantity of lipid in the final product since the most accurate quantitative measure of liposomes is in terms of lipid quantities. For a given lipid quantity, different liposome types will yield different quantities of liposome. Therefore, similar initial ratios of EGF to lipid for different liposome types should not be expected to yield the same level of binding. Another factor which would yield different results for different liposomes even under the same initial EGF to lipid ratios, is the differences in particle size, therefore in curvature, number and accessibility of PE sites on the surface of the liposome. Therefore, comparisons among liposome types should be avoided.

The effects of the increase in the EGF/lipid ratios in the presence of a crosslinking reagent are shown below in Tables 1 and 2. Generally, an increase in the level of binding occurs with the increase in initial EGF/lipid ratios regardless of which crosslinking reagent is used. At the lower end of the EGF/lipid ratios, the level of covalent binding increases significantly. Beyond initial concentration ratios of 25 ng EGF/uMoles lipid, the increase of binding is less significant. Noncovalently bound product is removed as excess unreacted material and does not appear in the reported results.

EXAMPLES

All of the following Examples using collagen, gelatin and EGF as the recognizing substances, were prepared according to the method described in Example One. Slight modifications, as described in the Examples, were required for the Examples using hyaluronic acid as the recognizing substance. The recognizing substances are assayed by traces of radioactive or fluorescent labels. Alternatively, the lipids are assayed by colorimetric methods. Determination of the protein recognizing substances can be done by the Lowry procedure, while free HA and liposome-bound HA can be determined by the Alcian Blue method.

Example One

EGF is added to a PE-liposome sample and the mixture is buffered by a phosphate buffer saline solution (PBS) to pH of 7.2. For drug-containing liposomes, drug encapsulation was performed in a swelling solution also of PBS. Concentration ratios of EGF to lipid are shown in Table 1. Aliquots from a 25% solution of the crosslinking reagent glutaraldehyde (GAD) are added at a ratio of 10 ul per 1 ml EGF/PE-liposome mixture. Incubation for a desired period (24–72 hours) is completed at either room temperature without stirring or at 37° C. with stirring. Depending upon the liposome used, excess unreacted material was removed, preferably through high speed centrifugation for one hour at 4° C. and 27000 xg or ultrahigh centrifugation for one to two hours, at 4° C. and 250000 xg followed by several repeated washings with EGF-free PBS. Column chromatography or dialysis against PBS may also be used in place of the centrifugation.

TABLE 1

| EGF-LIPOSOME CROSSLINKING BY GAD | | |
|---|---|---|
| | ngEGF/uMOLE LIPID (a) | |
| LIPOSOME TYPE | INITIAL | FINAL |
| MLV | 0.080 | 0.009 |
| MLV | 0.309 | 0.006 |
| MLV | 0.347 | 0.016 |
| MEL | 0.071 | 0.004 |
| MEL | 0.106 | 0.009 |
| MEL | 0.141 | 0.025 |
| LUVET | 0.016 | 0.003 |

(a) EGF assayed by a radioactive tracer.

Example Two

EGF is crosslinked with PE-liposome samples following the same procedure as in Example 1. Concentration ratios of labeled EGF to lipid are shown in Table 2.

TABLE 2

EGF-LIPOSOME CROSSLINKING BY GAD

| LIPOSOME TYPE | ng EGF/uMOLES LIPID (a) | |
|---|---|---|
| | INITIAL | FINAL |
| MLV | 0.26 | 0.07 |
| MLV | 0.78 | 0.16 |
| MLV | 1.60 | 0.21 |
| MLV | 6.00 | 0.31 |
| MLV | 24.70 | 0.35 |

(a) EGF assayed by a fluorescent tracer.

Example Three

Reaction mixtures of EGF and PE-liposomes were prepared as above and buffered by PBS to pH 7 or by 0.5N carbonate buffer to pH 9. Concentrations ratios of EGF to lipid are shown in Table 3. The crosslinking reagent EGDE was added in 0.2–1.0 ml volumes to buffered reaction mixtures of 2.5–3.0 ml volumes. Incubation periods were completed for 10–24 hours at 37° C. with stirring. Depending upon the liposome used, excess unreacted material was removed through high speed centrifugations and washings or dialysis against PBS.

TABLE 3

EGF-LIPOSOME CROSSLINKING BY EGDE

| LIPOSOME TYPE | ng/EGF/uMOLE LIPID (a) | | pH | mg EGDE |
|---|---|---|---|---|
| | INITIAL | FINAL | | |
| MLV (b) | 0.45 | 0.0078 | 9 | 500 |
| MLV | 3.72 | 0.90 | 9 | 500 |
| MEL | 0.10 | 0.012 | 9 | 500 |
| MEL | 0.10 | 0.0098 | 9 | 1000 |
| MEL (a) | 0.12 | 0.0022 | 7 | 200 |
| MEL | 1.78 | 0.47 | 9 | 500 |

(a) EGF assayed by a radioactive tracer.
(b) Initial ratios were increased by decreasing lipid concentration.

From these results, the preferred pH of 9 and quantity of crosslinking reagent of 500 mg has been determined.

Example Four

Gelatin was crosslinked to PE-liposomes following the same procedure as in Example One.

TABLE 4

GELATIN-LIPOSOME CROSSLINKING BY GAD

| Liposome Type | ugGelatin/uMole Lipid | | Incubation Period (a) |
|---|---|---|---|
| | Initial | Final | |
| MEL | 21 | 0.02 | Short |
| MEL | 63 | 0.24 | Short |
| MEL | 127 | 0.26 | Short |
| MEL | 21 | 15 | Long |
| MEL | 23 | 14 | Long |
| MEL | 25 | 18 | Long |
| MEL | 63 | 43 | Long |
| MEL | 187 | 208 | Long |
| MLV | 18 | 0.24 | Long |
| MLV | 66 | 0.67 | Long |
| MLV | 281 | 2.6 | Long |
| MLV | 556 | 6.4 | Long |
| MLV | 1140 | 13 | Long |
| MLV | 2350 | 13 | Long |
| MLV | 3440 | 24 | Long |
| MLV | 5830 | 26 | Long |

(a) Incubation Periods: "Short" is 5 minutes; "Long" is 24–48 hours.

Example Five

Collagen is crosslinked to PE-MLV samples with GAD following the same procedure as in Example 1 except incubation was at 4° C., at "Long" incubation periods.

TABLE 5

COLLAGEN-LIPOSOME CROSSLINKING BY GAD

| Liposome Type | ugCollagen/uMole Lipid | |
|---|---|---|
| | Initial | Final |
| MLV | 1.64 | 0.90 |
| MLV | 2.06 | 1.18 |
| MLV | 5.01 | 2.20 |
| MLV | 8.96 | 5.07 |
| MLV | 9.83 | 6.78 |
| MLV | 9.86 | 6.02 |
| MLV | 10.68 | 8.20 |
| MLV | 18.79 | 11.55 |
| MLV | 20.00 | 14.14 |

Example Six

Aqueous solutions of HA was pre-activated by incubation with water-soluble carbodiimide, EDC. The components were mixed to yield a preparation system of HA and EDC each at final concentrations of 1.7 mg/ml. The pH of the preparation system was adjusted to 3 by titration with 1N HCl. The preparation system was incubated for a variety of time periods at 37° C. with stirring. Table 6 shows an example of variation in the pre-incubation time period for reacting HA with EDC. A pre-incubation period of 3 hours is preferred to activate the carboxylic residues of HA.

TABLE 6

EFFECTS OF PRE-INCUBATION
HA-LIPOSOME BINDING(a)

| PRE-INCUBATION PERIOD (Hours) | mg HABound/mmole Lipid |
|---|---|
| 0 | 0 |
| 1 | 0 |
| 3 | 22.8 ± 0.9 |
| 24 | 20.9 ± 2.8 |

(a) Liposomes are LUVET or MLV. Incubation of the complete reaction mixture was for 24 hours, at 37° C., pH 3 with the addition of borate buffer.

After the pre-incubation period, PE-liposome samples were added and followed by the addition of a 0.1M borate buffer at pH 8.5. The HA/PE-liposome mixture was incubated at 37° C. in a shaker bath for 24 hours. Removal of excess unbound HA and reagents was by ultracentrifugation and washings. Initial and final concentrations of HA/lipid are reported in Table 8.

Example Seven

Various parameters affect the successful binding of HA to PE-liposomes when using EDC as the crosslinking reagent. These parameters include a pre-incubation procedure, pH of the reaction mixture, use of buffer solution in the incubation system and the contact area between liposomes and HA. Tables 7 and 8 provide data on variations of these parameters.

TABLE 7

EFFECTS OF pH, BUFFER PRE-INCUBATION AND CONTACT AREA ON COVALENT BONDING OF HA AND LIPOSOMES[a]

| pH | Borate Buffer | HA-Liposome Contact Area | mg HA Bound/ mmole Lipid |
|---|---|---|---|
| 4.5[b] | — | Narrow | 3.1 ± 0.6 |
| 4.5 | — | Narrow | 5.2 ± 0.5 |
| 4.5 | — | Wide | 7.6 ± 3.9 |
| 4.5 | Added | Wide | 19.0 ± 0.9 |
| 3.0 | Added | Wide | 26.5 ± 0.9 |

[a]Using MLV and EDC, three hours of pre-incubation (see exception below), 24 hours incubation of complete reaction mixture, both at 37° C.
[b]No pre-incubation, pH listed is for the incubation of the complete reaction mixture.

Example Eight

A reaction mixture of HA, dimethyl sulfoxide (DMSO) and acetic anhydride were stirred at room temperature for 24 hours. At the end of this period, the mixture was transferred to a dialysis sac and dialyzed against water over 48 hours. Activated HA was completely recovered from the sac as determined by the Alcian Blue method. Activated HA was incubated with PE-liposomes in 0.5M carbonate buffer at a pH of 9 for 24 hours in a shaker bath at 37° C. Adding sodium borohydride as a reducing agent, portions of the activated HA/PE-liposome mixture were incubated for an additional two hours. Removal of excess unbound HA and reagents was by centrifugation and washings. Concentration ratios of activated-HA to lipid are shown in Table 8.

TABLE 8

COVALENT BINDING OF HA TO LIPOSOMES CROSSLINKER-HA & ACTIVATED-HA (a)

| Methodology | mg HA/mmoles Lipid Initial | Final |
|---|---|---|
| Crosslinking With EDC | 1000 | 27 |
| HA Activation with DSMO/acetic anhydride, with reduction | 974 | 86 |
| HA Activation with DSMO/acetic anhydride, without reduction | 974 | 113 |

(a) Liposomes were MLV

The covalent bonding of the recognizing substances, gelatin, collagen, hyaluronic acid and EGF to liposomal surfaces can be achieved. Noncovalently bound product is removed as excess unreacted material and does not appear in the reported results. Preferably, protein-recognizing substances such as gelatin, collagen, and EGF are covalently bonded to PE-liposomes through amine residues with the crosslinking reagent GAD.

The bonding of hyaluronic acid to PE-liposomes can be completed either in the presence or absence of a crosslinking reagent. In the presence of a reagent, preferably EDC, a pH of 3 in the pre-incubation system is preferred. A 3-hour approximate time period is preferred for pre-incubation of the hyaluronic acid and crosslinking reagent. The addition of a 0.1M borate buffer at pH of 8.5 to the incubation system offers a positive contribution to the binding step. Changing the reaction mixture vessel in the binding step from test tubes to flasks, thereby increasing the area of contact between liposomes and hyaluronic acid did not adversely effect the binding results. Bonding of hyaluronic acid to PE-liposomes without a crosslinking reagent is preferably completed by pre-activation of hyaluronic acid and an incubation period of 24 hours at a reaction mixture pH of 9.

Example Nine

To compare the binding ability of regular liposomes and bioadhesive liposomes, A431 cell cultures were grown in monolayers, in flasks, applying usual procedures for this cell line. Two to three days prior to an experiment, the cells were seeded into multiwell culture plates and the experiments were done when the systems were confluent.

For purposes of assaying the modified liposomes, the EGF-recognizing substance was labeled with a generally known radioactive marker. Preparation of EGF-modified LUVET was completed as previously discussed.

Prior to the addition of a reaction mixture of EGF-modified liposomes, free liposomes or free EGF, media was removed from the A431 cells and the cells were washed with a binding buffer. The reaction mixture and cells were incubated for 1–2 hours, at room temperature. Upon dilution and withdrawal of the reaction mixture at the end of incubation, 2–3 successive washings with a binding buffer, of the wells were completed. Lysis of cells or detachment of cells from the wells was then followed by withdrawal and collection of the well content, denoted as the cell fraction. Assays of the cell fraction were completed by label counting of the fraction as compared with the counting of the immediate products created through the preparation process.

Figure 1:
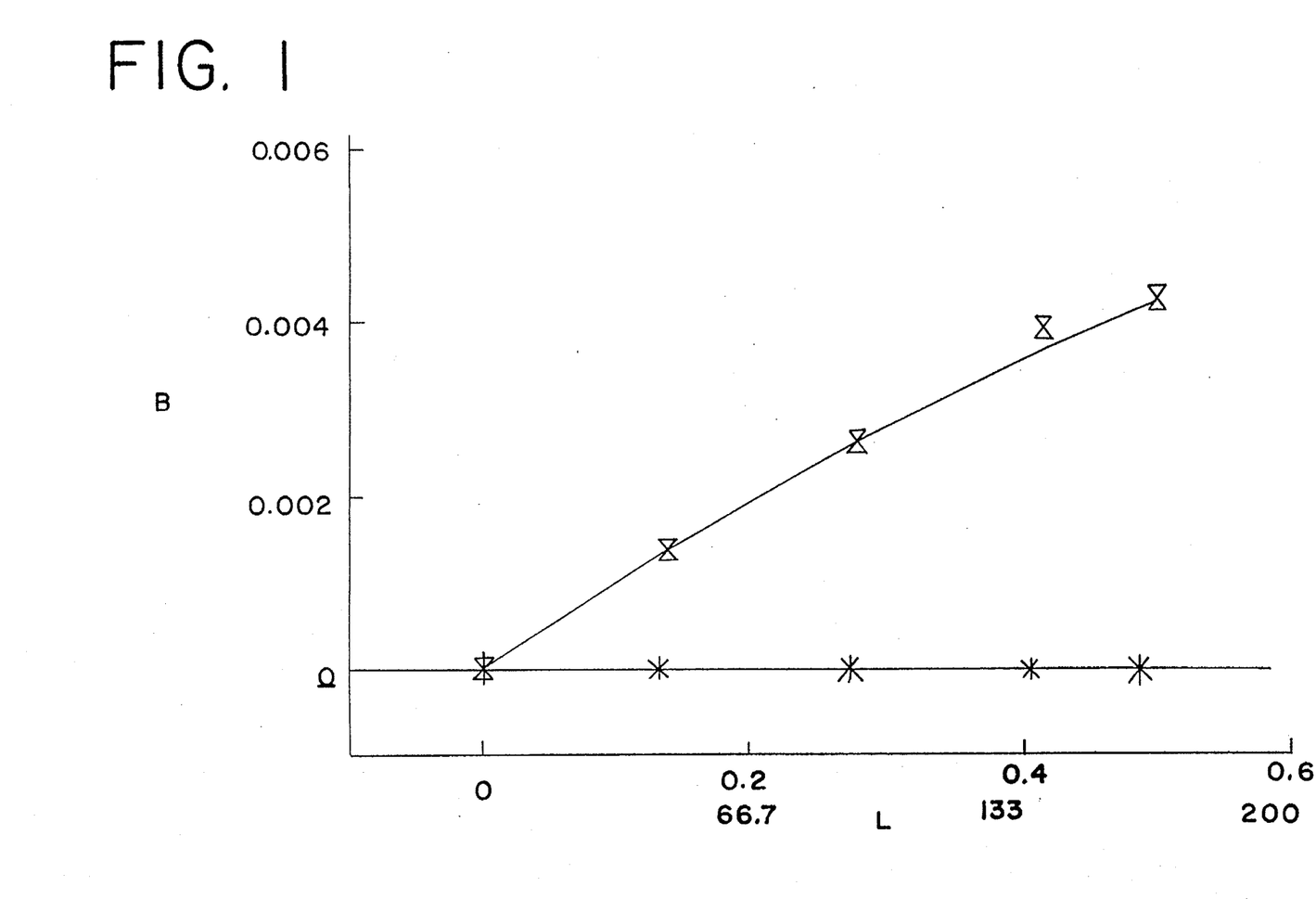
FIG. 1 shows the binding of bioadhesive liposomes (EGF-modified; open double triangle) and regular liposomes (asterisk) of the LUVET type to A431 cells in culture (in monolayers), as dependent upon liposome concentration. Bound liposomes, denoted as B, are in units of ng EGF per $10^6$ cells. Free ligand concentration, denoted as L, are in units of ng EGF per $10^6$ cells for bioadhesive liposome (first row of L values) and in units of umoles lipid per $10^6$ cells for the regular liposomes (second row of L values).

A comparison between the binding of free liposomes and EGF-modified liposomes to the A431 cells is illustrated in FIG. 1. The EGF-modified liposomes adhere to the A431 cells considerably better than free liposomes as no free liposomes were found at cell fraction. It is speculated that if free liposomes do associate with the cells, the dilution brought by the washings is sufficient to cause quantitative dissociation.

Example Ten

Binding studies of EGF-modified liposomes to A431 cells were carried out as described in Example 9 and the data were processed according to equation (1) above. The experimental conditions were such that the contribution of non-specific binding was negligible. Indeed, the data were found to fit unambiguously with a single type of binding site for each liposome system studied. Results for several systems are listed in Table 9.

TABLE 9

BINDING PARAMETERS OF BIOADHESIVE LIPOSOMES TO A431 CELLS IN CULTURE

| BIOADHESIVE LIPOSOME SYSTEM | $K_d$ (nM) | SITES PER CELL ($\times 10^{-5}$) |
|---|---|---|
| EGF-MLV | 0.60 ± 0.017 | 0.17 ± 0.03 |
| EGF-MLV | 5.03 ± 1.9 | 1.07 ± 0.03 |
| EGF-LUVET | 2.91 ± 0.003 | 0.18 ± 0.001 |
| EGF-MEL | 0.04 ± 0.007 | 0.042 ± 0.0042 |
| EGF-MEL | 0.40 ± 0.13 | 3.7 ± 0.90 |
| EGF-MEL | 0.48 ± 0.05 | 0.28 ± 0.01 |

Each bioadhesive liposome system is a different preparation; recognizing substance in each system is EGF.

An EGF-modified liposome is considerably larger than and different from free EGF, which is expected to affect the binding parameters. For a given class of receptors, the magnitudes of the dissociation constants for EGF-modified liposome systems are expected to be similar to or higher than those of free EGF. For a given class of receptors, the number of receptors per cell that are available for the EGF-modified liposomes is expected to be equal to or lower than the number of available for free EGF. Based on these considerations, the binding data of the present example fit with the receptor classes of ultra-high and high affinities.

Regardless of the specific cell-associated binding entity involved, the binding data listed in Table 9 show that EGF-modified liposomes bind to this cellular system with high affinity and with a sufficient number of sites for these modified liposomes to perform as the desired bioadhesive liposomes.

Example Eleven

Figure 2:
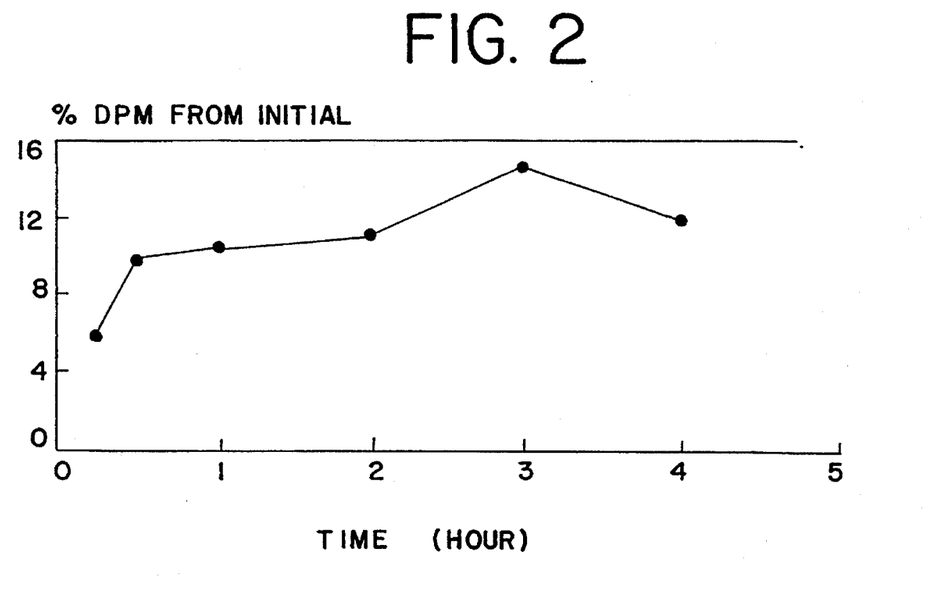
FIG. 2 shows a time course of the binding of bioadhesive liposomes (collagen-modified) of the MLV type to A431 cells in culture (in monolayers). Collagen is tritium-labeled. The fraction of liposomes relative to the amount present in the initial reaction mixture at zero-time which is cell-associated is determined over time.

Binding collagen-modified liposomes to A431 cells was carried out essentially according to the procedures detailed above. The A431 cell line is not known to contain receptors for collagen. The interaction of either free collagen or liposomally bound collagen with the A431 cell line is expected to result from association of collagen with components within the extracellular matrix. Referring to FIG. 2, incubation periods up to 4 hours were completed with 3 hours being the optimal period for binding.

Figure 3:
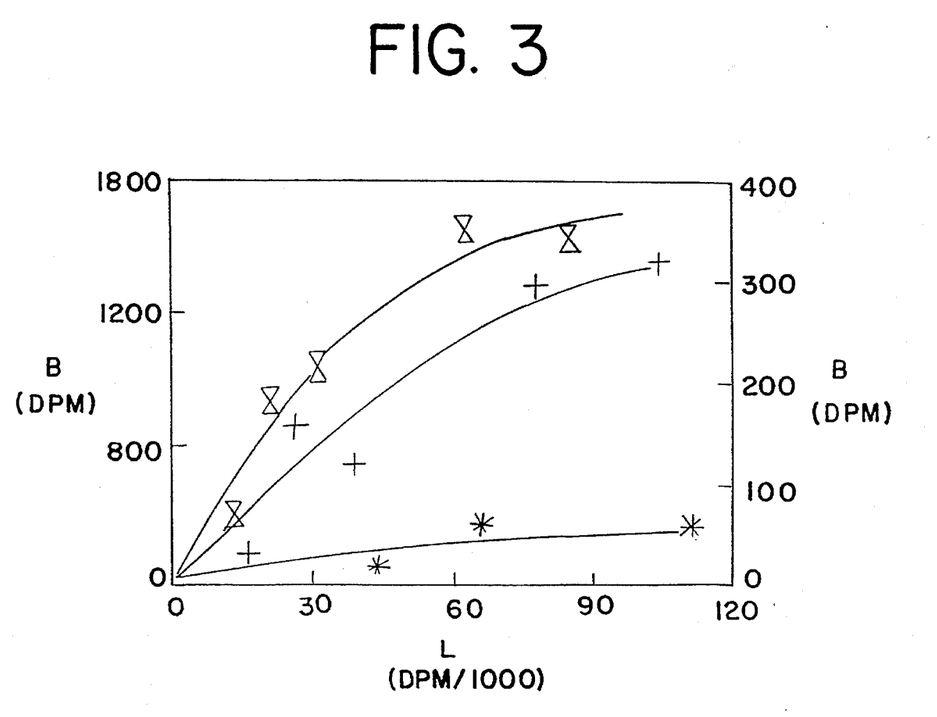
FIG. 3 shows the binding of bioadhesive liposomes (collagen-modified) and regular liposomes of the MLV type to A431 cells in culture (in monolayers). Collagen is tritium-labeled ($^3$-H) and liposomes are $^{14}$-C labeled. Bound liposomes, denoted as B, are in units of $^3$-H DPM per $10^5$ cells (left scale) and in units of $^{14}$-C DPM per $10^5$ cells (right scale). Free ligand concentration, denoted as L, are in units of $^3$-H or $^{14}$-C DPM per $10^5$ cells. Bioadhesive liposome with collagen labeled is depicted with open double triangles; bioadhesive liposome with the liposome labeled is depicted with crosses; and, regular liposome is depicted with asterisks.

Quantitative evaluations of binding of collagen-modified liposomes to A431 cells in culture are compared to regular liposome and exemplified in FIG. 3. The data were processed according to equation (1) above. Through double labeling, 3-H-collagen and 14-C-cholesterol, it was possible to monitor the collagen and liposome simultaneously. The binding of the collagen-modified liposomes to the cells is greater than the binding of the corresponding regular liposomes.

For free and collagen-modified liposomes, the binding entities are of the extracellular matrix type of cell-associated entity. As in the case of EGF-modified liposomes discussed in Example 10, the dissociation constant for collagen-modified liposomes is expected to be similar to or higher than those of free collagen. Likewise, the number of available sites in the extracellular matrix available for collagen-modified liposomes is expected to be similar to or lower than free collagen. The example given in Table 10 fits with these considerations. The data for free collagen demonstrate that binding of this bioadhesive recognizing substance to this cellular system does occur and is a measurable phenomena, which can be processed to yield quantitative and meaningful parameters. Moreover, the data in Table 10 show quite clearly that the binding of collagen-modified liposomes to this cellular system is of sufficiently high affinity and with a large enough number of sites, for the collagen-modified liposomes to perform as the desired bioadhesive liposomes.

TABLE 10

BINDING PARAMETERS OF FREE RECOGNIZING SUBSTANCES AND BIOADHESIVE LIPOSOME TO A431 CELLS IN CULTURE

| BIOADHESIVE LIPOSOME SYSTEM | $K_d$ (uM) | NUMBER OF SITES ($\times 10^{-5}$) |
|---|---|---|
| FREE COLIAGEN | 8.5 ± 2.3 | 179 ± 11 |
| COLLAGEN-MLV | 67.6 ± 31.35 | 548 ± 160 |

The bioadhesive liposomes of this invention are designed to perform as site-adherent, site-retained, sustained drug release depots. In vivo, the dynamics of the biological system can prematurely detach a drug delivery system from its target site. The dynamics in question are cellular dynamics due to proliferation, migration and demise of cells in the area to which the delivery system adheres. This type of dynamics may be seen in wounds, burns and tumors. The second dynamic is fluid dynamics due to the flow of body fluids over an area where the bioadhesive liposome may adhere. Effects of fluid dynamics are expected to vary depending on the bodily location and disease being treated. For example, the flow is relatively slow in therapeutic targets, such as wounds, mild in a target such as the peritoneal cavity and fast in a target such as the ocular area. In addition, in producing the bioadhesive liposomes of the present invention, it was important to determine whether the addition of the recognizing substance to the surface of the liposome would interfere with release of the encapsulated drug. Examples Twelve and Thirteen demonstrate the usefulness of bioadhesive liposomes as sustained release depots, in that attachment of the desired recognizing substance does not interfere with release of the encapsulated drug, in this case, the antibiotic Cefazolin. Examples Fourteen and Fifteen focus on the site-retainability of bioadhesive liposomes in view of cellular and fluid dynamics, respectively.

Example Twelve

Multilamellar liposomes (MLV), at a concentration of 30 mg/ml were prepared as described in previous Examples with one modification: in order to preserve drug stability, all incubations and procedures of the Cefazolin-containing systems were performed at 5° C. Cefazolin, at a concentration of 15 mg/ml was introduced into the system through the PBS swelling solution. The liposomes were incubated with EGF and with GAD, in the PBS buffer, as previously described. The reaction mixture was constantly stirred for 48 hours at 5° C. At the end of the incubation, the liposomes were separated from excess unbound EGF and byproducts by high speed centrifugation for one hour at 4° C. and 27000 xg. The liposome pellet was subjected to three consecutive washes which consisted of suspending the pellet in PBS containing 15 mg/ml Cefazolin and centrifuging as above. The drug was included in the wash buffer in order to prevent loss of the encapsulated drug in the process. Control (i.e., regular, non-bioadhesive) Cefazolin-encapsulated liposomes were prepared according to the same procedure without the addition of the recognizing substance.

The kinetics of Cefazolin release from these EGF-modified bioadhesive liposomes as well as from the control liposomes were studied, and the data processed, according to the following equation:

$$f = f_1 * (1-\exp(-k_1 t)) + f_2 * (1-\exp(-k_2 t))$$

wherein "f" denotes the fraction of the total drug in the system present in the dialysate at time=t, $k_1$ and $k_2$ are the rate constants for diffusion of the unencapsulated and the encapsulated drug, respectively, and $f_1$ and $f_2$ are the initial (i.e., at zero time) distributions (in fractions) of the total drug in the system, between the unencapsulated and the encapsulated pools, respectively, $f_1$ and $f_2$ sum to unity. The data fit the case of two drug pools, one of encapsulated drug and a second of unencapsulated drug. The results showing drug encapsulation efficiency and rate constant for release of the encapsulated drug were as follows: for the control liposomes encapsulation efficiency was 54(±11)%, and the rate constant for release of the encapsulated drug was 0.19(±0.004)hours$^{-1}$. For the bioadhesive liposome the encapsulation efficiency was 71(±7)%, and the rate constant for release of the encapsulated drug was 0.21(±0.0005)hours$^{-1}$.

Example Thirteen

Cefazolin-encapsulated multilamellar liposomes were prepared as described above. For surface modification into bioadhesive liposomes, the liposomes were incubated with collagen and GAD, in the PBS buffer which also contained 15 mg/ml Cefazolin. The reaction mixture was constantly stirred for 24 hours at 5° C. Two sets of liposomes were prepared. In Set I, the final concentrations were 25 mg/ml lipid, 2 mg/ml collagen and 10 ul/ml glutaraldehyde. In Set II, the liposome concentration was 150 mg/ml. At the end of the incubation, the liposomes were separated from the excess unbound collagen and byproducts by high speed centrifugation for one hour at 4° C., 27000 xg. For each Set, the liposomal pellet was subjected to three consecutive washings which consisted of suspending the pellet in PBS containing 15 mg/ml Cefazolin and centrifuging as described before. For Set I, the final pellet was suspended in PBS buffer plus Cefazolin, while for Set II, the final pellet was suspended in drug-free PBS.

The kinetics of Cefazolin release was studied as described previously. The data fit the case of two drug pools: one of encapsulated drug, and a second of unencapsulated drug. The parameters determined for Set I were: (a) the fraction of liposome-encapsulated Cefazolin at time zero was 52(±3)%, which in this case, was also the encapsulation efficiency; and, (b) the rate constant for release of the encapsulated drug was 0.033(±0.013)hours$^{-1}$. The parameters for Set II were: (a) the fraction of liposome-encapsulated Cefazolin at time zero was 81(±1)%; and, (b) the rate constant for release of the encapsulated drug was 0.0093(±0.0009)hours$^{-1}$.

The results of these two Examples indicate: (1) the method of creating bioadhesive liposomes can be carried out at low temperatures, thereby expanding the range of drugs which can be encapsulated and delivered in bioadhesive liposome systems; and, (2) the surface modification of the liposome through the addition of a recognizing substance, does not impair the ability of the liposome to release its encapsulated drug, thereby creating a sustained release depot in a bioadhesive liposome. In addition, Example Thirteen shows that the liposome concentration can be used as a tool to manipulate the rate of release of the encapsulated drug, going from a half-life of 0.88 days to a half-life of 3.1 days upon an increase in the liposome concentration. Based on these findings, such antibiotic-encapsulating bioadhesive liposomes are suitable for use in the topical treatment of infected wounds and burns, as well as, in other topically and regionally accessible injury- and non-injury-related infections, with the ability to match the rate of drug release to the requirements of the therapy, through selection of the liposome dose range.

Example Fourteen

Bioadhesive liposomes having hyaluronic acid as the bioadhesive ligand, were prepared as previously described. Monolayers of A431 cell line, seeded in 24-well culture plates using known procedures, serve as models for the in vivo areas to which the liposomes are designed to adhere and retain. The bioadhesive liposomes were incubated with the cell monolayers in complete cell growth media, at 37° C., for a period of 28 hours, which is well beyond the incubation period of 2–3 hours needed to attain equilibrium binding. At designated periods, the media in several wells was aspirated and the wells were washed three times with PBS at pH 7.2, containing 0.2% BSA. The cells were detached from the wells through trypsinization and subjected to the following assays: (1) determination of the number of viable cells/well, using Trypan Blue Method; and, (2) determination of the quantity of cells (or monolayer)-associated liposomes using radioactive counting. The results appear in Table 11 below.

TABLE 11

| DETERMINATION OF CELL-ASSOCIATED LIPOSOMES | | |
|---|---|---|
| Time Periods (hours) | Levels of Viable Cells/Well (× 10$^5$) | Bound Liposomes (nmoles of lipid/10$^5$ viable cells) |
| 0 | 3.77(± 0.52) | N/D |
| 1 | 3.4(± 0.73) | 12(± 2) |
| 4 | 2.7(± 0.59) | 34(± 7) |
| 11 | 2.2(± 0.27) | 37(± 8) |
| 23 | 2.9(± 0.86) | N/D |
| 28 | 4.4(± 0.93) | 34(± 9) |

The data above indicate that once the liposome binding reaches equilibrium (within 2–3 hours), the level of bound liposomes remains constant despite the cellular events taking place, i.e., demise, proliferation, migration of the cells. The data provide direct experimental support of the ability of the bioadhesive liposomes to be retained at a site to which they will be administered, despite cellular dynamics, a significant attribute of the bioadhesive liposomes.

Example Fifteen

Bioadhesive liposomes having hyaluronic acid as the recognizing substance and the A431 cell culture they bound to, were prepared according to the procedure described in Example Fourteen.

Figure 4:
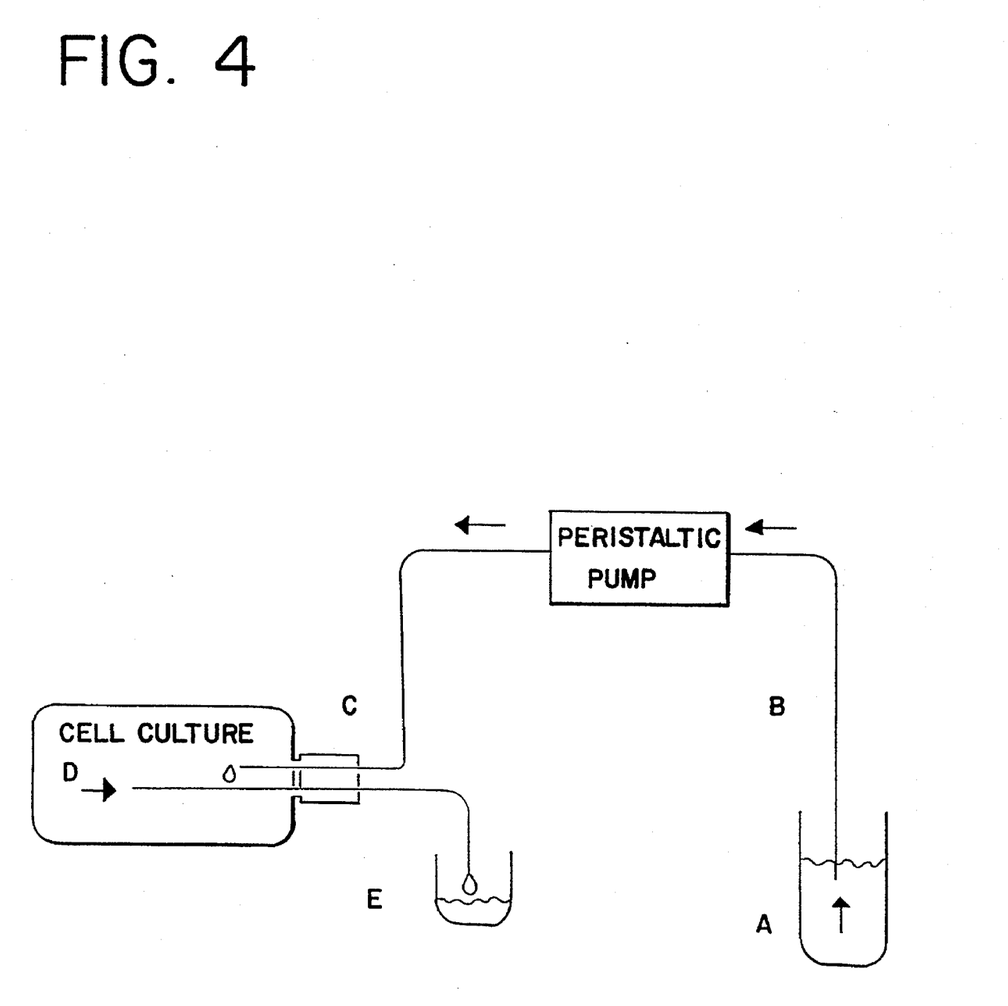
FIG. 4 shows a schematic drawing of the experimental setup for studying the effects of fluid dynamics on cultures of adherent cells having bioadhesive liposomes attached thereto.

To test the effects of fluid dynamics on site retention required an experimental setup which would make it possible to flow fluid at a controlled rate and for designated periods over a monolayer of cells to which the liposomes are bound. The designed setup, as shown in FIG. 4, included a peristaltic pump connected to a culture flask containing a monolayer of cells, using aseptic conditions. Selection of the rate of fluid to which the area of interest is exposed, will depend upon the specific liposomal system tested and on the future therapeutic objective. The object of this Example was to determine whether fluid dynamics put site-retention in a given cell-liposome system at risk at all, by deliberately testing at a high fluid flow rate. The flow rate was set at 0.64 ml/minute, using phosphate-buffered saline containing 0.2% bovine serum albumin, at a pH of 7.2. A flow rate of 1 minute sufficed for removal of more than 90% of the liposomes that remained unbound at equilibrium. This was completed by additional incremental removals of 4% and 2% brought about by flows of 5 minutes and 10 minutes, respectively, leaving the liposomes that were bound at equilibrium attached to the cell monolayer. Increasing the flow time beyond 10 minutes (for example, to 15 minutes) did not generate any additional removal of liposomes from the cell monolayer.

A second experiment compared the retention of regular (non-bioadhesive) liposomes to bioadhesive liposomes, after a 10 minute flow rate of 0.64 ml/minute. The retention of bioadhesive liposomes was found to be at least 2 fold higher than that of regular liposomes.

The above data clearly indicate that the bioadhesive liposomes of the present invention possess the ability to be retained at the site to which they will be administered, for prolonged periods of time despite fluid dynamics. Furthermore, the data indicate that once the fraction of liposomes that remain unbound at equilibrium is removed, the bioadhesive liposomes remain bound to the cell monolayer at a level close to the equilibrium binding, surviving exposure to continuous fluid flow at a rate well above the dynamics of body fluids expected in the biological targets. This feature enhances the novel delivery and retention ability of the bioadhesive liposomes of the present invention.

While the preferred embodiments have been described, various modifications and substitutes may be made without departing from the scope of the invention. For example, the pre-activation of the carboxylic residues of hyaluronic acid could be completed with dicyclohexylcarbodiimide or with N,N'-disuccinimidyl carbonate. Additionally, the mouse EGF and human urogastrone used in the disclosed examples could be substituted with growth factors from other natural or synthetic sources. Accordingly, it is to be understood that the invention has been described by way of illustration and not limitation.

I claim:

1. A process for covalently bonding a recognizing substance which is hyaluronic acid to a liposome creating a bioadhesive liposome comprising the steps of:
   (a) providing a reaction vessel containing a liposome having phosphatidylethanolamine;
   (b) activating the hyaluronic acid by pre-incubation in acidic pH with a crosslinker;
   (c) admixing the activated hyaluronic acid to the reaction vessel;
   (d) buffering the reaction mixture of the liposome and the activated hyaluronic acid to a basic pH;
   (e) incubating the buffered reaction mixture for a period of time sufficient for the bioadhesive liposome to form.

2. The process of claim 1 wherein the hyaluronic acid may be activated with a mixture consisting of DMSO and acetic anhydride at an acidic pH.

* * * * *

UNITED STATES PATENT AND TRADEMARK OFFICE
CERTIFICATE OF CORRECTION

PATENT NO. : 5,603,872
DATED : February 18, 1997
INVENTOR(S) : Rimona Margalit

It is certified that error appears in the above-indentified patent and that said Letters Patent is hereby corrected as shown below:

Column 11, line 7, delete "(x 10-5)" and replace with -- $(x\ 10^{-5})$ --.

Signed and Sealed this

Seventh Day of October, 1997

Attest:

BRUCE LEHMAN

Attesting Officer

Commissioner of Patents and Trademarks